(12) United States Patent
Rytky et al.

(10) Patent No.: US 11,219,408 B2
(45) Date of Patent: Jan. 11, 2022

(54) METHOD AND SYSTEM FOR DETERMINING TIME WINDOW FOR SLEEP OF A PERSON

(71) Applicant: NIGHT TRAIN OY, Oulu (FI)

(72) Inventors: Juha Rytky, Oulu (FI); Timo Partonen, Helsinki (FI); Liisa Kuula-Paavola, Espoo (FI); Anu-Katriina Pesonen, Helsinki (FI)

(73) Assignee: NIGHT TRAIN OY, Oulu (FI)

( * ) Notice: Subject to any disclaimer, the term of this patent is extended or adjusted under 35 U.S.C. 154(b) by 387 days.

(21) Appl. No.: 16/327,755

(22) PCT Filed: Aug. 21, 2017

(86) PCT No.: PCT/FI2017/050582
§ 371 (c)(1),
(2) Date: Feb. 22, 2019

(87) PCT Pub. No.: WO2018/037156
PCT Pub. Date: Mar. 1, 2018

(65) Prior Publication Data
US 2019/0183415 A1    Jun. 20, 2019

(30) Foreign Application Priority Data
Aug. 25, 2016    (FI) ................................. 20165631

(51) Int. Cl.
*A61B 5/00* (2006.01)
*A61B 5/01* (2006.01)

(52) U.S. Cl.
CPC .......... *A61B 5/4812* (2013.01); *A61B 5/0008* (2013.01); *A61B 5/01* (2013.01);
(Continued)

(58) Field of Classification Search
CPC ....... A61B 5/4812; A61B 5/0008; A61B 5/01; A61B 5/4857; A61B 5/4809; A61B 5/4815; A61M 21/02
(Continued)

(56) References Cited

U.S. PATENT DOCUMENTS 7,041,049 B1 *  5/2006  Raniere .................. A61M 21/02
                                            128/905
7,722,249 B2 *  5/2010  Kim ........................ G01K 1/024
                                            374/208
(Continued)

FOREIGN PATENT DOCUMENTS

CN    105814419 A    7/2016
EP    2 120 712 A2   11/2009

OTHER PUBLICATIONS

Kraeuchi K et al.: "Functional Link Between Distal Vasodilation and Sleep-Onset Latency?", American Journal of Physiology: Regulatory, Integrative and Comparative Physiol, American Physiological Society, US, vol. 278, Jan. 1, 2000 (Jan. 1, 2000), pp. R741-R748, XP008037952, ISSN: 0363-6119.
(Continued)

*Primary Examiner* — May A Abouelela
(74) *Attorney, Agent, or Firm* — Nixon & Vanderhye

(57) ABSTRACT

Disclosed is a method and a system implementing the method for determining an optimal time window for sleep of a person. The method includes receiving samples of a distal skin temperature of the person, and detecting a temperature change pattern in the samples of distal skin temperature. The temperature change pattern indicates a reference point within the circadian rhythm. The optimal time window for sleep is determined on the basis of the indicated reference point. The temperature change pattern is in the form of a drop in the distal skin temperature followed an increase in
(Continued)

the distal skin temperature, where the drop and the increase occur within a time window of ten minutes or less.

6 Claims, 1 Drawing Sheet

(52) U.S. Cl.
CPC .......... *A61B 5/4806* (2013.01); *A61B 5/4857* (2013.01); *A61B 5/4809* (2013.01)

(58) Field of Classification Search
USPC ........................................................ 600/549
See application file for complete search history.

(56) References Cited

U.S. PATENT DOCUMENTS

| | | | |
|---|---|---|---|
| 9,294,732 B2* | 3/2016 | Gillette | H04N 7/18 |
| 9,395,792 B1* | 7/2016 | Kahn | G06F 1/1698 |
| 9,474,876 B1* | 10/2016 | Kahn | A61B 5/4812 |
| 9,968,293 B1* | 5/2018 | Kahn | A61B 5/11 |
| 10,365,168 B2* | 7/2019 | Ban | G01K 1/20 |
| 10,561,376 B1* | 2/2020 | Kahn | G01J 1/429 |
| 10,791,986 B1* | 10/2020 | Kahn | A61B 5/0002 |
| 2005/0190065 A1* | 9/2005 | Ronnholm | G04G 21/025 340/575 |
| 2005/0209511 A1* | 9/2005 | Heruth | A61N 1/36135 600/301 |
| 2005/0209512 A1* | 9/2005 | Heruth | A61M 5/14276 600/301 |
| 2007/0191692 A1* | 8/2007 | Hsu | A61B 5/4815 600/301 |
| 2008/0146866 A1* | 6/2008 | Arai | A61B 5/4809 600/26 |
| 2008/0234785 A1* | 9/2008 | Nakayama | G01K 13/20 607/62 |
| 2010/0100004 A1* | 4/2010 | van Someren | A61B 5/1118 600/549 |
| 2010/1000004 | 4/2010 | Van | |
| 2010/0204764 A1 | 8/2010 | Garetz | |
| 2012/0029308 A1* | 2/2012 | Paquet | A61B 5/7282 600/301 |
| 2013/0310658 A1* | 11/2013 | Ricks | A61B 5/02055 600/301 |
| 2014/0121557 A1* | 5/2014 | Gannon | G01K 1/024 600/549 |
| 2015/0080756 A1* | 3/2015 | Robinson | A61B 5/1118 600/549 |
| 2015/0105687 A1 | 4/2015 | Abreu | |
| 2015/0128353 A1* | 5/2015 | Kildey | A47C 27/082 5/706 |
| 2015/0313474 A1* | 11/2015 | Goto | A61B 5/7235 600/549 |
| 2016/0071393 A1 | 3/2016 | Kaplan et al. | |
| 2016/0073788 A1* | 3/2016 | Franceschetti | A47C 21/00 219/486 |
| 2016/0228060 A1 | 8/2016 | Mazar et al. | |
| 2016/0330311 A1* | 11/2016 | Du | G06F 1/1694 |
| 2016/0331244 A1* | 11/2016 | Barton-Sweeney | A61B 5/024 |
| 2017/0035351 A1* | 2/2017 | Prerau | A61B 5/369 |
| 2017/0094046 A1* | 3/2017 | Raymann | A61B 5/4809 |
| 2017/0156594 A1* | 6/2017 | Stivoric | A61B 5/14532 |
| 2017/0281119 A1* | 10/2017 | Stroman | A61B 5/002 |
| 2017/0347948 A1* | 12/2017 | Thein | A61B 5/02416 |
| 2017/0360360 A1* | 12/2017 | Alqurashi | G06F 19/00 |
| 2018/0028111 A1* | 2/2018 | Waris | A61B 5/4815 |
| 2018/0070840 A1* | 3/2018 | Cronin | A61B 5/6824 |
| 2018/0125418 A1* | 5/2018 | Haakma | A61B 5/4812 |
| 2018/0177975 A1* | 6/2018 | Goto | A61B 5/4809 |
| 2018/0192873 A1* | 7/2018 | Chausiaux | A61B 5/746 |
| 2018/0214028 A1* | 8/2018 | Zhang | A61B 5/4318 |
| 2018/0330811 A1* | 11/2018 | Macary | G06Q 50/12 |
| 2019/0251824 A1* | 8/2019 | Yamawaki | A61B 5/4809 |

OTHER PUBLICATIONS

Raymann et al.: "Skin temperature and sleep-onset latency: Changes with age and insomnia", Physiology and Beha, Elsevier Science Ltd., Oxford, GB, vol. 90, No. 2-3, Feb. 1, 2007 (Feb. 1, 2007), pp. 257-266, XP005869357, ISSN: 0031-9384, DOI: 10.1016/J.PHYSBEH.2006.09.008.

Seward B Rutkove et al.: "A methodology for the real-time measurement of distal extremity temperature; The real-time distal extremity temperature measurement", Physiological Measurement, Institute of Physics Publishing, Bristol, GB, vol. 28, No. 11, Nov. 1, 2007 (Nov. 1, 2007), pp. 1421-1428, XP020130200, ISSN: 0967-3334.

International Search Report, dated Nov. 7, 2017, from corresponding PCT/FI2017/050582 application.

FI Search Report, dated Mar. 15, 2017, from corresponding FI 20165631 application.

Office Action issued in Chinese Patent Application No. 201780051608.9 dated Mar. 5, 2021.

* cited by examiner

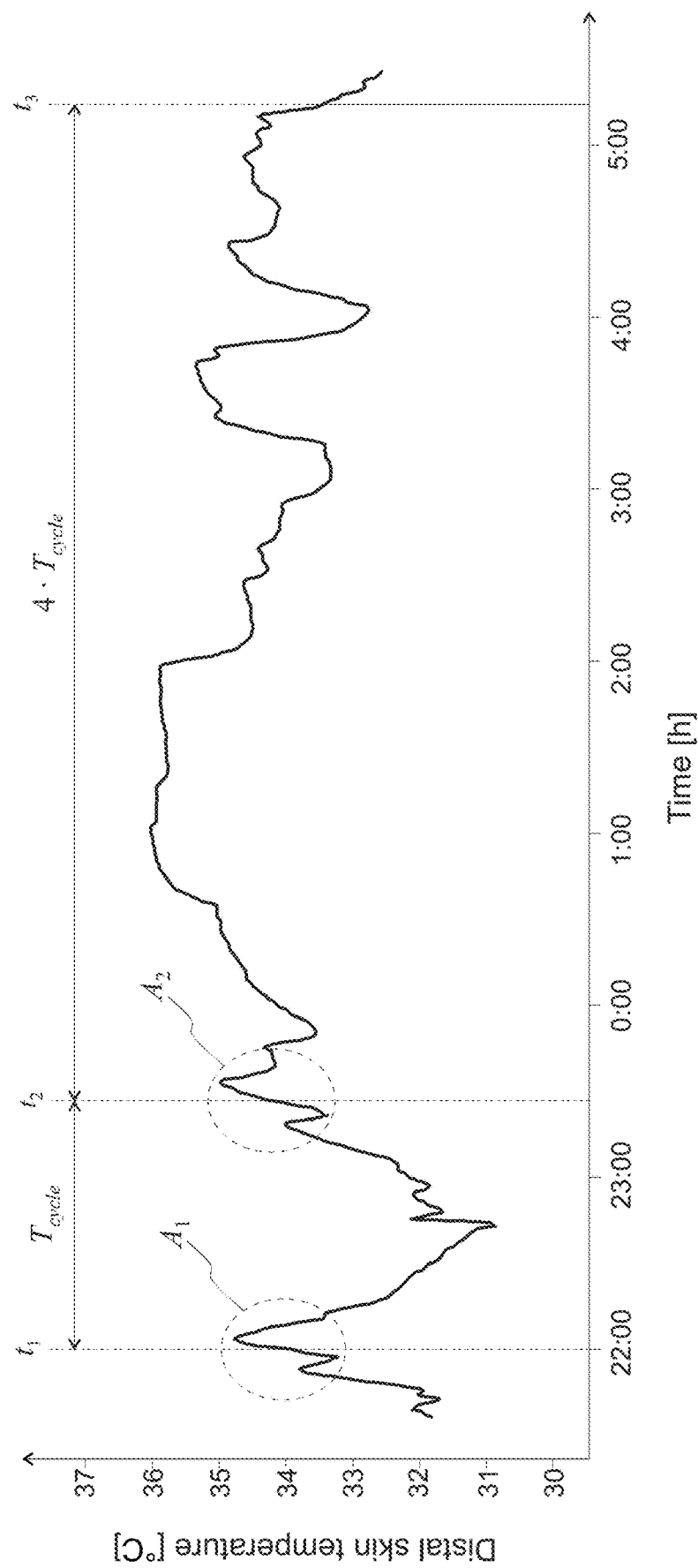

METHOD AND SYSTEM FOR DETERMINING TIME WINDOW FOR SLEEP OF A PERSON

FIELD

The present disclosure relates to monitoring of sleep of a person and more particularly to determining ultradian cycles within a circadian rhythm of the person.

BACKGROUND

Sleep of a human follows a circadian rhythm, i.e. a sleep-wakefulness cycle that is on average 24.09±0.2 h (24 h 5 min±12 min) for women and 24.19±0.2 h (24 h 11 min±12 min) for men, aged 18 to 74 years. The circadian rhythm is typically synchronized to the day-night cycle, i.e. the light-darkness cycle. During sleep within the circadian rhythm, a natural sleep cycle repeats itself at a constant interval reflecting the 1-to-2-hour ultradian basic rest-activity cycle. The natural sleep cycle comprises a plurality of stages including light sleep, deep (slow wave) sleep, and REM (Rapid Eye Movement) sleep that repeat in a predetermined order.

An adult person may be considered to need on average a minimum of 4 full sleep cycles that are guided by the human circadian system controlling the core temperature rhythm and the sleep-wake cycle. Less sleep may result in various negative effects to wellbeing and health. In order to ensure sufficient amount of sleep for a person, it may be desirable to try to monitor the sleep and to estimate the progress of the person's natural sleep cycles.

Estimates of the progress of the natural sleep cycles may be based on the nightly movements of a person, for example. The movements may be estimated by using a microphone to detecting noises caused by the movements or by using an accelerometer. However, the magnitude and content of the measured data may be highly dependent on the positioning of the sensors. Further, the measurements are easily interfered (e.g. by another person sleeping in the vicinity of the monitored person). Measurement of core temperature of the person can provide fairly accurate information on the progress of the circadian rhythm. However, measurement of the core temperature during the sleep of a person may be impractical and uncomfortable.

BRIEF DISCLOSURE

An object of the present invention is to provide a method and system for implementing the method so as to alleviate the above disadvantages. The objects of the invention are achieved by a method and a system which both are characterized by what is stated in the independent claims. The preferred embodiments of the invention are disclosed in the dependent claims.

An optimal time window for sleep of a person can be accurately detected by monitoring distal skin temperature. There is a direct link between production of melatonin (and other hormones related to sleep) and the circadian rhythm. Once the level of melatonin in the blood stream of the person reaches a certain level after start of nocturnal melatonin production, a rapid, distinct pattern can be observed in the distal skin temperature of the person. The distal skin temperature first drops and thereafter rises again rapidly. Said pattern occurs approximately within ten minutes, typically within five minutes.

The temperature change pattern provides a fixed reference point within the circadian rhythm. It indicates an optimal time for going to sleep. Once a person has fallen asleep, the natural sleep cycle repeats at a constant interval from the start of the sleep. Based on the starting point of the sleep and the constant interval, it is possible to accurately determine the progress of the natural sleep cycles. With this information, it is possible to optimize the instant for getting to sleep and/or for waking up.

Since the temperature change pattern indicating the optimal starting point for sleep is fast and distinctive, the measurement of the distal skin temperature does not have to be very accurate. These rapid changes of the distal skin temperature are easy to identify as they are much faster and greater in a short time period than so called normal skin temperature changes caused by activities, such as walking and running, or changes in ambient temperature. The skin temperature may thus be measured with or without contact to the skin. This enables accurate, robust, and comfortable approaches for determining the optimal time window for sleep.

BRIEF DESCRIPTION OF THE DRAWINGS

In the following the invention will be described in greater detail by means of preferred embodiments with reference to the attached drawings, in which FIG. 1 illustrates an exemplary diagram of distal skin temperature during ultradian cycles within the circadian rhythm.

DETAILED DISCLOSURE

The present disclosure describes a method for determining an optimal time window for sleep of a person. The method comprises receiving samples of a distal skin temperature of the person and detecting a temperature change pattern in the samples of the distal skin temperature. The samples may originate from a temperature sensor arranged to measure the distal skin temperature. In this context, distal skin temperature refers to skin temperature at extremities of body, such as the limbs and the head of a person. For example, in the context of the present disclosure, distal skin temperature may be measured from a finger, wrist, ankle, forehead or ear lobe.

There is a direct link between production of melatonin and the circadian rhythm. At the same time, melatonin production has a correlation with distal skin temperature. A rapid, distinct pattern in the distal skin temperature can be observed after the nocturnal melatonin production has started. Then, the distal skin temperature falls approximately by 0.5° C., after which the distal skin temperature rises by approximately 1.5° C. This temperature change pattern is rapid: it typically occurs within approximately 10 minutes (typically within about 5 minutes).

FIG. 1 shows an exemplary curve of distal skin temperature of a person. In FIG. 1, rapid skin temperature change indicates the optimal time window for sleep to open, also called as a "sleep train". An optimal time to go to sleep is within 20-30 minutes from the characteristic temperature change pattern that follows the start of nocturnal melatonin production. When the person falls asleep, sleep cycles start to run, distal skin temperature of the person starts to rise steadily, and the temperature change patterns cease to occur. If the person does not go to sleep, the temperature pattern repeats itself after a period. FIG. 1 shows two temperature change patterns: a first pattern $A_1$ at 21:55 and a second pattern $A_2$ at 23:23. In other words, the person does not fall asleep after the first pattern $A_1$ in FIG. 1. However, after the second pattern $A_2$, the person falls asleep, and his/her distal skin temperature rises about 2° C. in about 60 minutes.

Sleep train frequency (i.e. the frequency of occurrences of the temperature change patterns) determines the length of each sleep cycle. The best time windows to wake-up are after four or five complete sleep cycles. In FIG. 1, the length $T_{cycle}$ of the sleep cycle (i.e. the time between the first pattern $A_1$ and the second pattern $A_2$) is 88 minutes. The length of the cycle multiplied by four ($1 \times T_{cycle}$ in FIG. 1) and starting from the second pattern $A_2$ (falling asleep when the distal skin temperature starts rising steadily) at the start of sleep results in an optimal wake-up instant at 05:15 in the morning in FIG. 1. Similarly, an optimal wake-up instant based on five sleep cycles would be at 6:43 in the morning.

Therefore, in order to track the optimal time window for sleep of a person, the distal skin temperature may be monitored for occurrences of the above-described temperature change patterns. For example, in a method according to the present disclosure, a temperature change pattern in the distal skin temperature monitored with a skin temperature sensor may be detected. The temperature change pattern indicates a reference point within the circadian rhythm. The method may be configured to detect a temperature change pattern that is in the form of a drop in the distal skin temperature followed an increase in the distal skin temperature, wherein the drop and the increase occur within a time window of ten minutes or less, for example five minutes. The magnitude of the increase is higher than the magnitude of the drop. The magnitude of the drop may be approximately 0.5° C. and the magnitude of the increase may be approximately 1.5° C., for example.

Presence of the temperature change pattern in the sampled distal temperature may be detected by using various different algorithms. For example, the distal skin temperature may be periodically sampled and the samples may be stored. Based on the samples, a method according to the present disclosure may determine if an above-described drop and following increase occur in a predetermined window of subsequent samples. Alternatively, the pattern may be detected by monitoring the rate of change (i.e. the slope) of the distal skin temperature. Various known pattern recognition algorithms may also be used for detecting the temperature change in the samples of the monitored distal skin temperature.

An optimal time window for sleep, determined on the basis of the temperature change pattern, may be utilized in various ways. For example, an optimal instant for turning in for sleep may be estimated on the basis of determined optimal time window for sleep. The ability to fall asleep may be considered to be linked to the start of production of melatonin. When the characteristic temperature change pattern is observed in the distal temperature of a person, he or she has approximately 20 to 30 minutes to get to sleep. Typically, the interval (i.e. length) of the natural sleep cycle is approximately 90 minutes for an adult, but it may vary between individuals. For example, depending on the age of the person, the length of the sleep cycle may vary between 40 minutes to 130 minutes. However, within a time frame of a day or several days, the interval at which the natural sleep cycle repeats itself may be considered to remain rather constant. By determining the interval between the occurrences of the temperature change patterns according to the present disclosure, an accurate estimate of the length of the natural sleep cycle of the person can be calculated. As a result, optimal instants for turning in may be predicted based on the detected occurrences of the temperature change patterns and the interval between occurrences. Based on the optimal instant for a wake-up or turning in to sleep has been determined, an alarm may be raised when the optimal instant is present. Once a person has fallen asleep, the temperature change patterns cease to occur. The temperature change patterns will re-start again if the person awakes in the middle of the night. This may be used as a further indicator of sleep when monitoring the sleep of a person. When she or he falls asleep, the distal skin temperature starts to increase constantly by about 2° C. in the forthcoming 120 minutes.

A method according to the present disclosure may also comprise estimating an optimal instant for a wake-up for a person on the basis of the determined optimal time window for sleep. An adult person may be considered to need 4 to 6 full sleep cycles. If a wake-up (e.g. in the form of an alarm) is scheduled to occur at a light sleep stage within the natural sleep cycle, the person wakes up feeling fresh and energetic. An optimal instant or instants of wake-up may be calculated on the basis of the characteristic temperature change patterns and length of the natural sleep cycle, for example. An optimal wake-up instant may be calculated by adding a plurality (e.g. 4, 5, or 6) of determined lengths of the natural sleep cycle (e.g. 90 minutes) to the time of the last observed occurrence of the characteristic temperature change pattern in the evening. Once the optimal instant has been reached, an alarm may be raised in order to wake up the person.

Because the temperature is so fast and distinctive, cost-effective, low-end measurement equipment may be used. The temperature change pattern may be detected with a MEMS-based temperature sensor or an infrared sensor, for example. The temperature sensor may be a part of a wearable device, for example. In order to be able to detect the change pattern, the distal temperature has to be sampled at a sufficient frequency. For example, the distal temperature may be sampled at least once a minute, e.g. once every 30 seconds.

In some embodiments, a method according to the present disclosure may further comprise monitoring movements and/or heart rate of the monitored person in order to improve the accuracy of the determination of the circadian rhythm. This additional information may be used for providing further confirmation on the estimated circadian rhythm and the stages of the natural sleep cycle during the circadian rhythm. The accuracy of the estimate of the circadian rhythm may be further improved by gathering data for a plurality of days and by using this data for calculating the estimate.

The present disclosure further discloses a detection unit and a system for determining an optimal time window for sleep of a person.

The detection unit may comprise means configured to receive samples of distal skin temperature, and carry out the steps of an above-described method according to the present disclosure. The detection unit may be a stand-alone apparatus or it may be a part of a larger system.

For example, the detection unit may be a stand-alone apparatus that comprises a sensor for measuring a distal skin temperature of a person, and means for implementing the method for determining the optimal time window for sleep according to the present disclosure. The apparatus may comprise control unit comprising a computing device (such as a processor, an FPGA, or an ASIC) and a memory which may act as the means for implementing the method. The control unit may be configured to receive samples of the measured distal skin temperature from the sensor and detect the temperature change pattern according to the present disclosure in the samples. The temperature change pattern indicates a reference point within the circadian rhythm. The optimal time window for sleep of the person may then be determined on the basis of the indicated reference point.

The stand-alone detection unit may be configured to estimate an optimal instant for a wake-up and/or an optimal instant for turning in for sleep on the basis of the determined optimal time window for sleep. The detection unit may implement a timer or clock function, and once an optimal instant has been reached, the detection unit may cause an alarm to be raised, in the form of an audible or visual cue, for example. The stand-alone detection unit may be in the form a wearable, such as an activity bracelet or a heart rate monitor, that comprises a temperature sensor for monitoring a distal skin temperature of the person. The wearable may be configured to implement also other functionalities in addition to a method according to the present disclosure.

In some embodiments, the detection unit may also be a part of a larger system for determining an optimal time window for sleep of a person. For example, a system for determining the optimal time window for sleep may comprise a separate measurement unit comprising a distal skin temperature sensor and a detection unit that configured to receive samples of distal skin temperature from the measurement unit.

The measurement unit may be separate from the detection unit and may comprise a wireless communication unit through which the distal skin temperature data is sent to the detection unit. The wireless connection unit may transmit samples of the distal skin temperature via Bluetooth, Zig-Bee, near field communication (NFC), or infrared protocols, for example. The measurement unit may be in the form of a garment or a wearable, such as an activity tracker, a smartwatches, an earbud, a rings, an e-stickers (i.e. an adhesive sensor), for example. If a wearable is already equipped with a skin temperature sensor, the method and system according to the present disclosure may be implemented without hardware changes to the wearable. In automotive or avionics applications, the measurement unit may be integrated to controls (e.g. to the driving wheel of a car).

The detection unit may be a generic computing device or system, for example. A method according to the present disclosure may be implemented in the form of a computer program product having instructions which, when executed by the computing device or system, cause the computing device or system to perform a method according to the present disclosure. For example, detection unit may be a handheld communication device, such as a smart phone or a tablet computer or even infotainment device or any kind of medical device, into which the computer program product is downloaded. The handheld communication device may be configured to wirelessly receive samples of distal skin temperature originating from the measurement unit, detect a temperature change pattern in the samples of distal skin temperature in order to indicate a reference point within the circadian rhythm, and determine the optimal time window for sleep of the person on the basis of the indicated reference point. The handheld communication device may further be configured to estimate an optimal instant for a wake-up and/or an optimal instant for turning in for sleep on the basis of the determined optimal time window for sleep, and raise an alarm on the basis of the estimated optimal instant.

Alternatively, cloud computing may be utilized for implementing the detection unit. For example, a cloud computing system may configured to receive samples of distal skin temperature of a person, detect a temperature change pattern in the samples of distal skin temperature in order to indicate a reference point within the circadian rhythm, and determine optimal time window for sleep of the person on the basis of the indicated reference point. The cloud computing system may further be configured to estimate an optimal instant for a wake-up and/or an optimal instant for turning in for sleep on the basis of the determined optimal time window for sleep, and cause an alarm to be raised on the basis of the estimated optimal instant. For example, the cloud computing system may send an indication to a handheld communication device that an alarm should be raised. The handheld communication device then raises an alarm on the basis of this indication.

Functionalities of the method according to the present disclosure may also be divided between a cloud computing system and a separate decision-making unit. For example, the may detect temperature change patterns as describe above, and send timing information on the detected temperature change patterns to a decision-making unit that determines the optimal time window for sleep on the basis of the timing information. The decision-making unit may be a handheld communication device, for example. The decision-making unit may be further configured to estimate an optimal instant for a wake-up and/or an optimal instant for turning in for sleep on the basis of the determined optimal time window for sleep, and raise an alarm on the basis of the estimated optimal instant.

The method (and a detection unit and system implementing the method) according to the present disclosure may be utilized in various applications. For example, the method may be used for implementing a driver's sleep alert in a vehicle, e.g. a car. The measurement of the distal temperature from hand of the driver may be integrated to the driving wheel, for example. Alternatively the measurement of a distal temperature may be implemented as an infrared sensor. The temperature data may be sent to a computing device integrated to the vehicle (e.g. on-board computer) or a handheld device, such as a smart phone.

The method according to the present disclosure may also be utilized in minimizing jet lag. For a human, it is possible to adjust the circadian rhythm approximately by one hour per day. With the method according to the present disclosure, this adjustment can be done in a systematic manner.

It is obvious to a person skilled in the art that the inventive concept can be implemented in various ways. The invention and its embodiments are not limited to the examples described above but may vary within the scope of the claims.

The invention claimed is:

1. A computer-implemented method for determining an optimal time window for sleep of a person, the method comprising:
   receiving samples of a distal skin temperature of the person;
   detecting a temperature change pattern in the samples of distal skin temperature, the temperature change pattern indicating a reference point for the optimal time window for sleep;
   determining the optimal time window for sleep based on the indicated reference point; and
   estimating one or more of (i) an optimal instant of a wake-up and (ii) an optimal instant of turning in for sleep based on the determined optimal time window for sleep,
   wherein the temperature change pattern is a drop in the distal skin temperature followed by an increase in the distal skin temperature, a magnitude of the drop being approximately 0.5° C., a magnitude of the increase being approximately 1.5° C., the drop and the increase occurring within a time window of ten minutes or less.

2. The method of claim 1, further comprising:
causing an alarm to be raised based on the estimated optimal instant of the wake-up or the estimated optimal instant of the turning in for sleep.

3. A detection system for determining an optimal time window for sleep of a person, the detection system comprising:
a controller configured to
receive samples of a distal skin temperature of the person,
detect a temperature change pattern in the samples of distal skin temperature, the temperature change pattern indicating a reference point for the optimal time window for sleep,
determine the optimal time window for sleep based on the indicated reference point, and
estimate one or more of (i) an optimal instant of a wake-up and (ii) an optimal instant of turning in for sleep based on the determined optimal time window for sleep,
wherein the temperature change pattern is a drop in the distal skin temperature followed by an increase in the distal skin temperature, a magnitude of the drop being approximately 0.5° C., a magnitude of the increase being approximately 1.5° C., the drop and the increase occurring within a time window of ten minutes or less.

4. The detection system of claim 3, wherein the controller is configured to
cause an alarm to be raised based on the estimated optimal instant of the wake-up or the estimated optimal instant of the turning in for sleep.

5. A system for determining an optimal time window for sleep of a person, the system comprising:
a measurement system comprising a distal skin temperature sensor and a wireless transmitter, and
the detection system of claim 3 that is configured to receive samples of the distal skin temperature from the measurement system.

6. A non-transitory computer-readable medium on which is stored a computer program having instructions which, when executed by a computer or computing system, cause the computer or computing system to execute a method of:
receiving samples of a distal skin temperature of a person,
detecting a temperature change pattern in the samples of distal skin temperature, the temperature change pattern indicating a reference point for an optimal time window for sleep,
determining the optimal time window for sleep based on the indicated reference point, and
estimating one or more of (i) an optimal instant of a wake-up and (ii) an optimal instant of turning in for sleep based on the determined optimal time window for sleep,
wherein the temperature change pattern is a drop in the distal skin temperature followed by an increase in the distal skin temperature, a magnitude of the drop being approximately 0.5° C., a magnitude of the increase being approximately 1.5° C., the drop and the increase occurring within a time window of ten minutes or less.

* * * * *